US012690874B2

(12) United States Patent
Schuele et al.

(10) Patent No.: US 12,690,874 B2
(45) Date of Patent: Jul. 28, 2026

(54) MEDICAL INSTRUMENT

(71) Applicant: Aesculap AG, Tuttlingen (DE)

(72) Inventors: Jana Schuele, Kreenheinstetten (DE);
Jian Zoing Tan, Tuttlingen (DE);
Christoph Rothweiler, Donaueschingen
(DE)

(73) Assignee: Aesculap AG, Tuttlingen (DE)

( * ) Notice: Subject to any disclaimer, the term of this
patent is extended or adjusted under 35
U.S.C. 154(b) by 198 days.

(21) Appl. No.: 18/294,083

(22) PCT Filed: Jul. 26, 2022

(86) PCT No.: PCT/EP2022/070889
§ 371 (c)(1),
(2) Date: Jan. 31, 2024

(87) PCT Pub. No.: WO2023/011976
PCT Pub. Date: Feb. 9, 2023

(65) Prior Publication Data
US 2025/0082340 A1 Mar. 13, 2025

(30) Foreign Application Priority Data

Aug. 3, 2021 (DE) ..................... 10 2021 208 392.7

(51) Int. Cl.
*A61B 17/128* (2006.01)
*A61B 17/29* (2006.01)
(52) U.S. Cl.
CPC ...... *A61B 17/1285* (2013.01); *A61B 17/2909*
(2013.01); *A61B 2017/2901* (2013.01); *A61B
2017/2946* (2013.01)
(58) Field of Classification Search
CPC ............ A61B 17/1285; A61B 17/2909; A61B
17/291; A61B 17/2912; A61B 17/2913;
(Continued)

(56) References Cited

U.S. PATENT DOCUMENTS

| 5,817,128 A | 10/1998 | Storz |
| 10,905,420 B2 | 2/2021 | Jasemian et al. |
| | (Continued) | |

FOREIGN PATENT DOCUMENTS

| DE | 10320477 | 7/2004 |
| DE | 4307539 A1 | 8/2005 |
| | (Continued) | |

OTHER PUBLICATIONS

Search Report received in International Application No. PCT/
EP2022/070889 dated Nov. 29, 2022, with translation, 6 pages.

*Primary Examiner* — Brooke Labranche
*Assistant Examiner* — Rachael L Geiger
(74) *Attorney, Agent, or Firm* — Christopher A. Rothe;
CM Law

(57) ABSTRACT

A medical instrument includes a handle with a fixed part, a
movable part, a locking device, a shaft releasably locked on
the handle by the locking device, and a jaw arranged on the
shaft. The jaw is movable between open and closed positions
by actuation of the movable part. A push-pull element is
guided in the shaft and operatively connected to the movable
part and to the jaw. The locking device has an actuation
element that is movable into a release position to release the
locking, and a blocking element which is connected to the
movable part and movable into a blocking position in a
working position of the movable part, in which the blocking
element blocks mobility of the actuation element, and which
is movable into an enabling position in a rest position of the
movable part, to permit mobility of the actuation element.

8 Claims, 6 Drawing Sheets

(58) Field of Classification Search
CPC .... A61B 2017/2901; A61B 2017/2902; A61B
2017/2903; A61B 2017/2905; A61B
2017/2946; A61B 2017/0046
See application file for complete search history.

(56) References Cited

U.S. PATENT DOCUMENTS

| | | | |
|---|---|---|---|
| 2009/0206123 A1* | 8/2009 | Doll ................ | A61B 17/07207 |
| | | | 227/175.1 |
| 2018/0116674 A1* | 5/2018 | Baril ............... | A61B 17/00234 |

FOREIGN PATENT DOCUMENTS

| | | | |
|---|---|---|---|
| EP | 3756572 | A2 | 12/2020 |
| JP | 2019513471 | A | 5/2019 |
| WO | 2017180746 | A1 | 10/2017 |

* cited by examiner

MEDICAL INSTRUMENT

CROSS-REFERENCE TO RELATED APPLICATIONS

This application is the United States national stage entry of International Application No. PCT/EP2022/070889, filed on Jul. 26, 2022, and claims priority to German Application No. 10 2021 208 392.7, filed on Aug. 3, 2021. The contents of International Application No. PCT/EP2022/070889 and German Application No. 10 2021 208 392.7 are incorporated by reference herein in their entireties.

FIELD

The invention relates to a medical instrument, in particular for applying medical clips, having a handle device with a fixed handle part, a movable handle part which is manually movable relative to the fixed handle part between a non-actuated rest position and an actuated working position, and with a locking device, an elongate shaft whose proximal end is releasably locked on the handle device by means of the locking device, an instrument jaw which is arranged on a distal end of the shaft and which is movable between an open position and a closed position by an actuation of the movable handle part, and having an elongate push-pull element which is guided axially movably in the shaft and which, for force and movement transmission, is operatively connected proximally to the movable handle part and distally to the instrument jaw.

BACKGROUND

A medical instrument of this kind is known from EP 0 688 187 B1 and is provided in the form of a medical forceps for use in endoscopic interventions. The known forceps has a handpiece with a fixed handle part and a movable handle part. Moreover, the medical forceps has an elongate shaft in the form of an outer tube, which is locked releasably on the handpiece. A pull rod, guided axially movably in the outer tube, is operatively connected at one end to a forceps jaw, mounted distally on the outer tube, and at the other end to the movable handle part. The outer tube can be disassembled, together with the forceps jaw and the pull rod, from the handpiece. This in particular for cleaning and sterilizing.

SUMMARY

The object of the invention is to make available a medical instrument of the aforementioned type which offers improved patient safety.

This object is achieved by the fact that the locking device has an actuation element which is movable manually into a release position in order to release the locking, and a blocking element which is operatively connected to the movable handle part and which is moved into a blocking position in the working position of the movable handle part, in which blocking position the blocking element interlockingly blocks the mobility of the actuation element, and which is moved into an enabling position in the rest position of the movable handle part, in which enabling position the mobility of the actuation element is enabled. The solution according to the invention prevents an uncontrolled release of the locking when the medical instrument is in a state not intended for this. The invention proceeds from the knowledge that release of the locking, particularly in an actuated state of the instrument, i.e. in the working position of the movable handle part, may have disadvantageous effects for the patient. By virtue of the solution according to the invention, release of the locking is prevented in the actuated working position. In this way, disadvantageous effects in the use of the instrument are avoided. This ultimately leads to improved patient safety. The movable handle part is preferably pivotable between its rest position and its working position relative to the fixed handle part. Alternatively or in addition, the movable handle part can be linearly movable relative to the fixed handle part. Preferably, the locking device is integrated in the fixed handle part. The locking device serves for releasably locking the shaft, hence also the further components connected to the shaft, for example the push-pull element and the instrument jaw, on the handle device. Preferably, the shaft is releasably connected to the handle device by form-fit and/or force-fit engagement, the locking device counteracting release of the connection and/or itself effecting the connection. Said connection between the shaft and the handle device can be designed, for example, as a screw-in, plug-in, latching and/or clamping connection. The shaft extends preferably in a straight line between its proximal end and its distal end. Preferably, the shaft is at least in part tubular and/or a hollow cylinder. The shaft can be of one piece or of multiple pieces. In the open position, the instrument jaw is opened. In the closure position, the instrument jaw is closed. Preferably, the instrument jaw is formed between two jaw parts which are movable relative to each other and which, in the closure position, are moved onto each other and, in the open position, are moved away from each other. The instrument jaw is operatively connected to the movable handle part indirectly via the push-pull element. An actuation of the movable handle part, in the working position of the latter, can either bring about an opening or a closing of the instrument jaw, the latter being preferred. Upon actuation of the movable handle part, the push-pull element can act on the instrument jaw with a pulling and/or pushing action, the latter being preferred. With a pulling action, the push-pull element functions as pulling element. With a pushing action, the push-pull element functions as pushing and/or thrust element. Between its proximal end and its distal end, the push-pull element is preferably straight and/or coaxial to the shaft. Preferably, the push-pull element is guided in the shaft interlockingly in the radial direction and with a sliding movement in the axial direction. An actuation of the movable handle part causes a movement of the blocking element into its blocking position. The movement of the blocking element between the enabling position and the blocking position can be by rotation and/or translation. The movement of the actuation element into the release position can be by rotation and/or translation. In the blocking position, the blocking element blocks the mobility of the actuation element into the release position, preferably directly and/or interlockingly. The medical instrument is preferably provided for use in laparoscopic operations. The medical instrument is, for example, preferably in the form of a medical forceps, a clamp, scissors or the like. Accordingly, the instrument jaw is, for example, a forceps jaw, clamp jaw or scissors jaw.

In one embodiment of the invention, the actuation element in the release position blocks the mobility of the blocking element into the blocking position and/or the mobility of the movable handle part into the working position. This prevents the movable handle part from being actuated when it is in a state not intended for this. This embodiment of the invention proceeds from the knowledge that an actuation of the movable handle part in the release position of the actuation element, i.e. during the release of the locking of the shaft, may have disadvantageous effects for the patient. This embodiment of the invention prevents actuation of the movable handle part during the release of the locking. In this way, further disadvantageous effects in the use of the medical instrument are avoided. This also prevents the actuation element from being blocked in its release position. This ultimately leads to further improved patient safety. The blocking of the mobility of the blocking element and/or of the movable handle part is preferably effected interlockingly and/or directly by means of the actuation element.

In a further embodiment of the invention, the blocking element is pretensioned with spring loading in the direction of the blocking position by a first spring element arranged on the handle device, and, in the locked state of the shaft, is pretensioned with spring loading in the direction of the enabling position by a second spring element arranged on the shaft, wherein the second spring element causes greater pretensioning than the first spring element. This particularly preferred embodiment of the invention affords further advantages. For further explanation, a distinction can be made between a first configuration and a second configuration of the medical instrument. In the first configuration, the shaft, hence also the push-pull element and the instrument jaw, is mounted on the handle device, i.e. connected to the latter and/or locked on the latter. In the second configuration, the shaft, hence also the push-pull element and the instrument jaw, is disassembled from the handle device, i.e. the connection and/or locking produced in the first configuration is released. The first configuration can also be designated as the assembly state. The second configuration can also be designated as the disassembly state. In the assembly state, the first spring element and the second spring element both act on the blocking element. The first spring element and the second spring element act in opposite directions, the second spring element being stronger than the first spring element. By virtue of the greater pretensioning that results from this, the blocking element in the assembly state is moved with spring loading into the enabling position. This at any rate when the movable handle part is in its rest position and does not additionally act on the blocking element. In the disassembly state, the second spring element, together with the shaft, is released from the handle device, such that the pretensioning of the blocking element into the enabling position is stopped. In this way, the blocking element is moved into the blocking position under the effect of the first spring element. On account of the operative connection of the blocking element to the movable handle part, the latter is preferably moved at the same time into the working position. As a result, in the disassembly state, the actuation element is at all times blocked. This ensures that the actuation element cannot be actuated during disassembly of the shaft.

This embodiment proceeds from the knowledge that unwanted and/or uncontrolled actuating of the actuation element during assembly of the shaft can have disadvantageous effects. These disadvantageous effects are ruled out by this embodiment of the invention. In this way, patient safety is improved still further. The first spring element is preferably integrated in the handle device. The second spring element is arranged on the shaft. In one embodiment, the first spring element and/or the second spring element acts directly on the blocking element. In a further embodiment, the first spring element and/or the second spring element acts indirectly on the blocking element. For example, the first spring element can act on the blocking element indirectly via the movable handle part. The second spring element can, for example, act on the blocking element indirectly via the push-pull element.

In a further embodiment of the invention, the actuation element is movable in the radial direction of the push-pull element, and the blocking element is movable in the axial direction of the push-pull element. This has design advantages in particular. On the one hand, the blocking function of the blocking element can be realized very simply in design terms. For example, the blocking element, for blocking the radial mobility of the actuation element, can be pushed under, over or against the actuation element. The blocking thus obtained is particularly robust. If a blocking of the mobility of the blocking element and/or of the movable handle part by means of the actuation element is additionally provided, the actuation element, in the axial direction of movement of the push-pull element, can be moved in front of or behind the latter. This outwards or inwards in the radial direction.

In a further embodiment of the invention, the actuation element is a push button which is able to be pressed into the release position, and the blocking element is a linearly movable slide which, in the blocking position, is slid at least partially under the push button. This embodiment of the invention is particularly easy to implement in design terms. At the same time, it permits particularly robust blocking of the mobility of the actuation element. In the release position, the push button is pushed at least partially in front of the slide. This permits simple and robust blocking of the mobility of the slide, and thus also of the movable handle part operatively connected to the slide. Preferably, the push button can be pretensioned with spring loading counter to a movement into the release position, this by means of a further spring element, which can also be designated as a third spring element. In one embodiment, the push button is movable in the radial direction of the push-pull element. In a further embodiment, the push button is movable in the axial direction of the push-pull element. The same applies, mutatis mutandis, to the mobility of the slide. Preferably, the push button and/or the slide is mounted movably on the fixed handle part.

In a further embodiment of the invention, the movable handle part is mounted on the fixed handle part pivotably about a pivot pin, and the blocking element has a driver pin which is oriented parallel to the pivot pin and which interacts with a driver groove introduced into the end face of the movable handle part. In this way, an operative connection between the movable handle part and the blocking element is achieved which is particularly simple in design terms and also particularly robust. The operative connection serves to transmit force and movement between the movable handle part and the blocking element. The pivot pin and/or the driver pin can be spatially and physically present in the form of a corresponding structural part or can be an axis in the geometric sense. Preferably, the driver pin, in the axial direction of the push-pull element, engages interlockingly in the driver groove and/or interlockingly about the pivot pin of the movable handle part. Preferably, the driver pin is received in the driver groove slidably about its circumferential direction.

In a further embodiment of the invention, the movable handle part acts on a proximal end of the push-pull element in a force-transmitting and movement-transmitting manner by way of the blocking element. Accordingly, in this embodiment of the invention, the blocking element has a particularly advantageous multiple function. On the one hand, the blocking element serves for said blocking of the mobility of the actuation element. On the other hand, the blocking element additionally acts as a mechanical transmission element between the movable handle part and the push-pull element. This permits a further simplified design. Preferably, the movable handle part is operatively connected to the push/pull element exclusively by means of the blocking element.

In a further embodiment of the invention, the blocking element has a distally arranged supporting portion on which the proximal end of the push-pull element is supported in the axial direction and/or is received interlockingly in the radial direction. An advantageous transmission of force and movement to the push-pull element is achieved through the support in the axial direction. Improved guiding of the push-pull element can be achieved through the interlocking in the radial direction. Preferably, the supporting portion has a form-fit profile, for example in the form of a hollow or a stub, which is releasably plugged together in the axial direction with the proximal end of the push-pull element in order to form the radial interlocking.

In a further embodiment of the invention, the locking device has a spring-loaded latch which in the axial direction engages interlockingly in a notch of the shaft and can be disengaged from the notch by the actuation element. In this embodiment of the invention, the locking is realized as a releasable latch-notch connection. The latch is operatively connected to the actuation element. In one embodiment, the latch is embodied as a structural part which is separate from the actuation element and which is connected to the latter to transmit force and movement. In another embodiment, the latch is a portion of the actuation element and is to this extent in one piece with the latter. The notch is arranged on the proximal end of the shaft. The notch is preferably designed as a depression extending in the circumferential direction of the shaft, for example as an annular groove. In the release position of the actuation element, the latch is disengaged from the notch. Otherwise, the latch is engaged in the notch. The engaging and/or disengaging movement of the latch is preferably oriented in the radial direction of the shaft and/or push-pull element.

BRIEF DESCRIPTION OF THE DRAWINGS

Further advantages and features of the invention will become clear from the following description of a preferred exemplary embodiment of the invention which is shown in the drawings.

DETAILED DESCRIPTION

Figure 1:
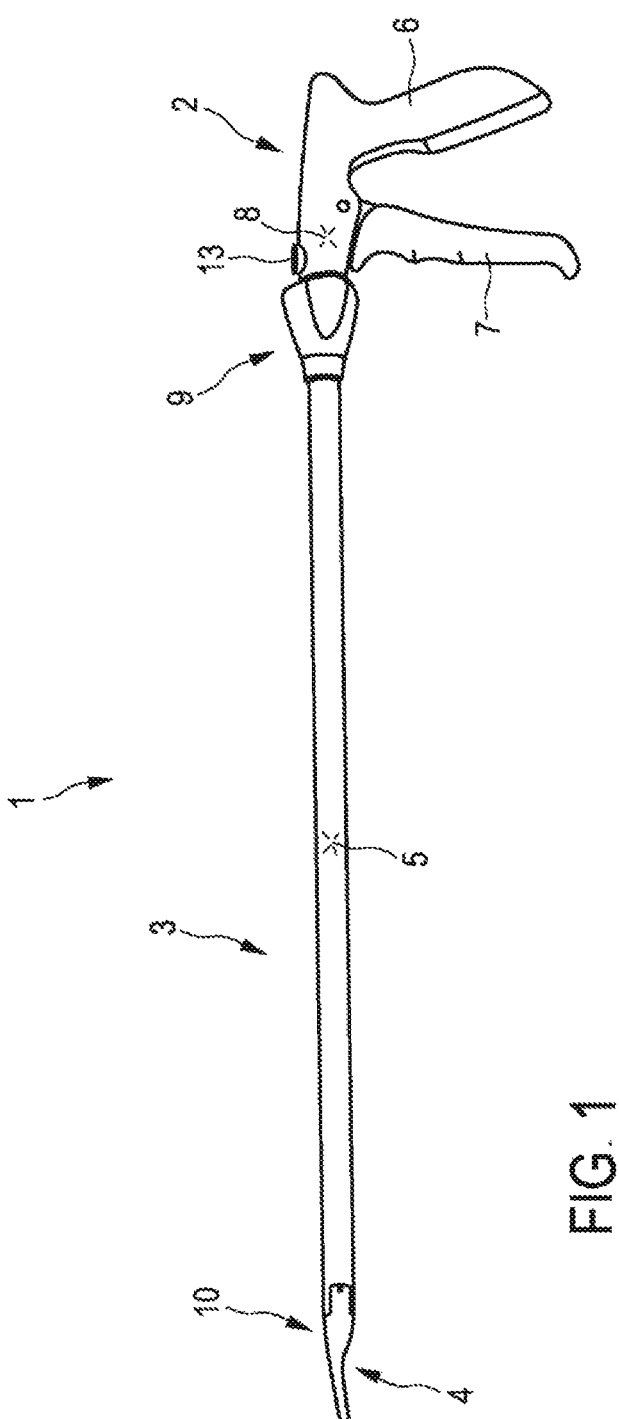
FIG. 1 shows a schematic side view of an embodiment of a medical instrument according to the invention with a handle device, a shaft mounted releasably on the handle device, and an instrument jaw mounted distally on the shaft.

According to FIG. 1, a medical instrument for use in laparoscopic operations is provided. In the present case, the medical instrument is in the form of a medical forceps 1. The medical forceps 1 is used to apply medical clips and can therefore also be designated as a medical clip applicator.

The medical forceps 1 has a handle device 2, an elongate shaft 3, an instrument jaw in the form of a forceps jaw 4, and a push-pull element 5.

The handle device 2 has a fixed handle part 6, a movable handle part 7 and a locking device 8. The movable handle part 7 is manually movable relative to the fixed handle part 6 between a non-actuated rest position (see FIGS. 1, 3 and 6) and an actuated working position (see FIG. 7).

The shaft 3 is elongate between a proximal end 9 and a distal end 10. In the configuration shown in FIG. 1, the medical forceps 1 is in an assembly state ready for use. In this assembly state, the shaft 3 is mounted, together with the forceps jaw 4 and the push-pull element 5, on the handle device 2. The proximal end 9 of the shaft 3 is releasably locked on the handle device 2 by means of the locking device 8, in a manner that will be described in more detail. The medical forceps 1 can be transferred to a disassembly state in which the handle device 2 is separated from the rest of the components of the medical forceps 1. For this purpose, said locking is releasable, in a manner that will be described in more detail.

The forceps jaw 4 is movable between a closed position (FIG. 1) and an open position (FIG. 2) by an actuation of the movable handle part 7. Accordingly, the forceps jaw 4 and the movable handle part 7 are operatively connected to each other for transmission of force and movement.

Figure 2:
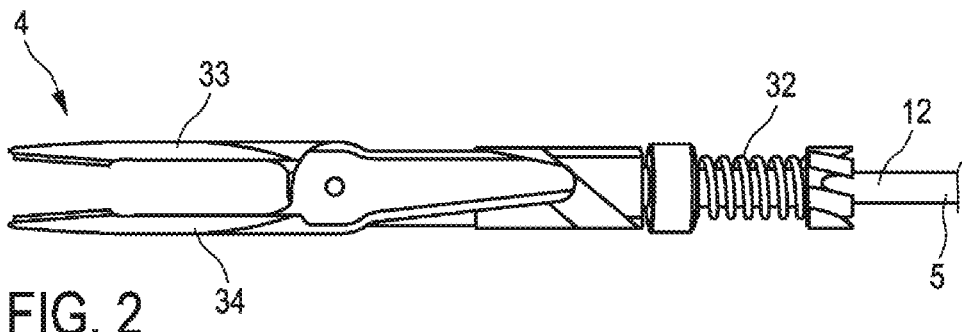
FIG. 2 shows a schematic, partially cutaway side view of a detail of the shaft in the region of the instrument jaw, with individual components and/or portions left out.

Said operative connection is established by means of the push-pull element 5. The push-pull element 5 is elongate between a proximal end 11 (FIG. 3) and a distal end 12 (FIG. 2). The proximal end 11 is operatively connected to the movable handle part 7. The distal end 12 is operatively connected to the forceps jaw 4. The push-pull element 5 is guided axially movably in the shaft 3. In the embodiment shown, the shaft 3 and the push-pull element 5 are oriented coaxially to each other.

To release the locking, the locking device 8 has an actuation element 13. The actuation element 13 is movable manually between a non-actuated rest position (in particular FIGS. 1, 3 and 4) and an actuated release position (not shown in detail in the drawings). In the rest position of the actuation element 13, the locking is active. In the release position of the actuation element 13, the locking is released or also cancelled. As soon as the locking is released, the handle device 2 and the shaft 3 can be separated from each other for the purpose of disassembly.

Figure 3:
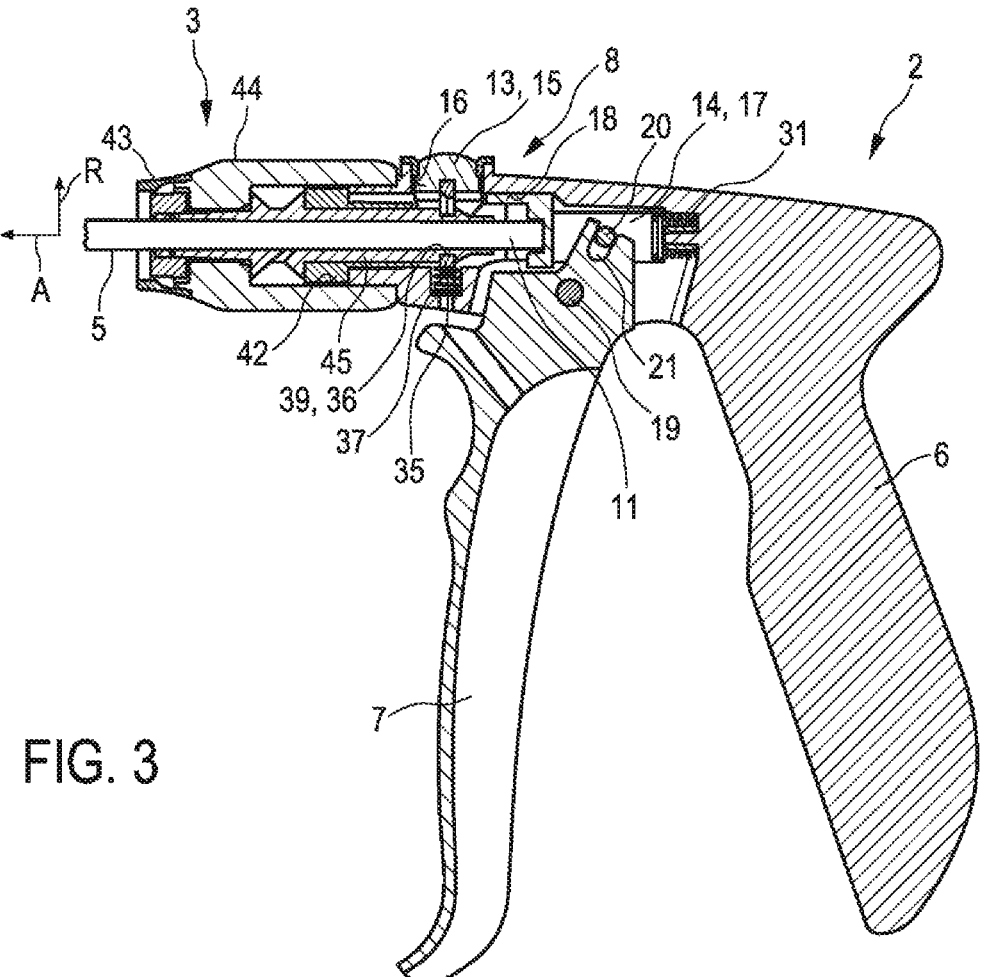
FIG. 3 shows a schematic, partially cutaway longitudinal sectional view of the medical instrument according to FIG. 1 in the region of the handle device.
Figure 6:
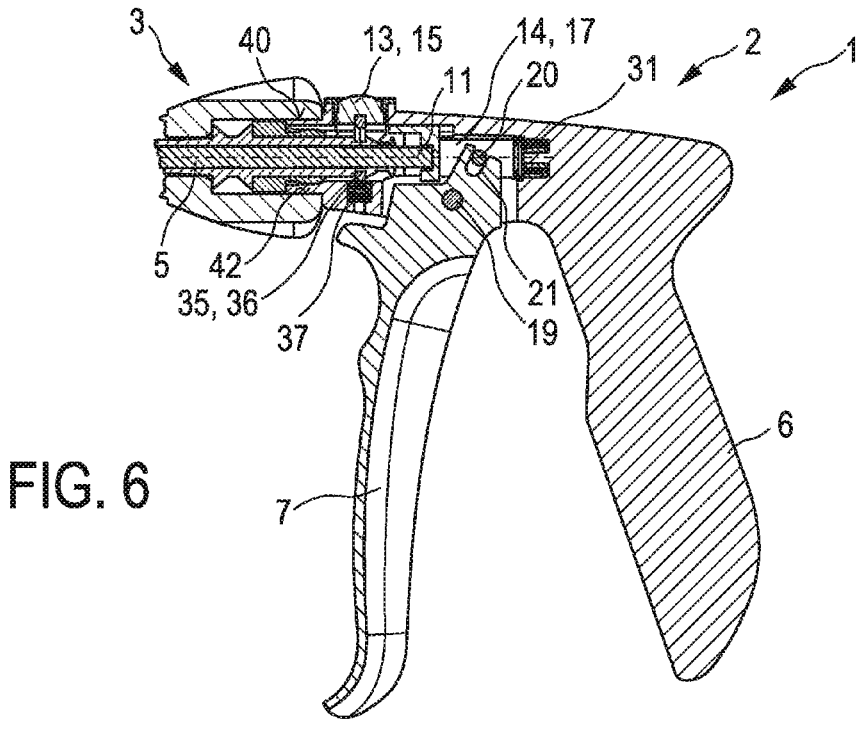
FIGS. 6 and 7 show partially cutaway, schematic longitudinal sectional views of the medical instrument in the region of the handle device, with a movable handle part of the handle device in a non-actuated rest position (FIG. 6) and an actuated working position (FIG. 7)
Figure 7:
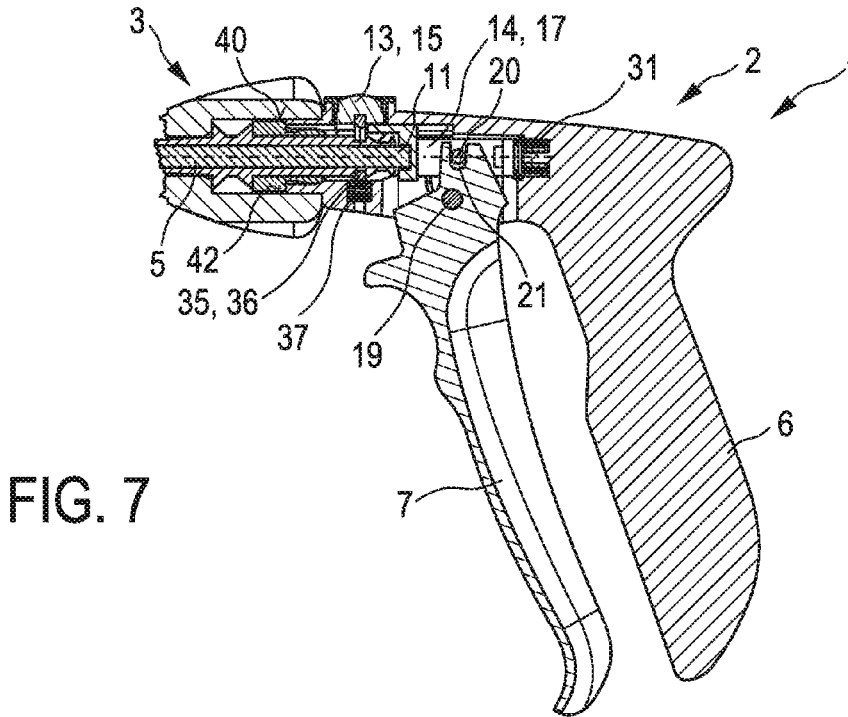

In order to avoid the locking being released when the medical forceps 1 is in a state not intended for this, the locking device 8 has a blocking element 14 (see FIG. 3). The blocking element 14 is operatively connected to the movable handle part 7. In other words, the blocking element 14 is movable according to the movement of the movable handle part 7 and/or vice versa. In the rest position of the movable handle part 7, the blocking element 14 adopts an enabling position (see FIGS. 3 and 6). In the working position of the movable handle part 7, the blocking element 14 adopts a blocking position (FIG. 7). In the blocking position, the mobility of the actuation element 13 into the release position is interlockingly blocked by means of the blocking element 14. In the enabling position, the mobility of the actuation element is unaffected by the blocking element 14 and is to this extent enabled. This prevents a situation where the locking is released in the actuated state of the medical forceps 1.

Further structural and functional features of the medical forceps 1 are explained in more detail below. The features explained below are to be regarded as advantageous. In terms of the present invention, however, the features explained below are not essential.

In the embodiment shown, the actuation element 13 is movable in the radial direction R of the push-pull element 5. The blocking element 14 is movable in the axial direction A of the push-pull element 5. Since the shaft 3 and the push-pull element 5 are oriented coaxially to each other in the embodiment shown, it is also possible to talk about the radial direction R of the shaft 3 and its axial direction A. In an embodiment not shown in the drawings, the mobility of the actuation element and of the blocking element can be different for this purpose. For example, the blocking element can be radially movable and the actuation element axially movable.

The actuation element 13, in its non-actuated rest position, is moved radially outwards and, in its actuated release position, is moved radially inwards. The blocking element 14, in its enabling position, is moved axially rearwards (proximally) and, in its blocking position, is moved axially forwards (distally). By contrast, in an embodiment not shown in the drawings, the release position is a radially outwardly relocated position of the actuation element. Accordingly, the blocking position can be a proximally relocated position of the blocking element.

In the embodiment shown, the blocking element 14 in the blocking position is slid at least partially under the actuation element 13, such that the latter cannot be moved inwards in the radial direction R (FIG. 7). The form-fit blocking of the actuation element 13 accordingly acts in the radial direction R.

In the present case, the actuation element 13 is a push button 15 that can be pressed in radially into the release position. The push button 15 is arranged on an upper face of the handle device 2. The push button 15 is received in a receiving recess 16 of the handle device 2. The push button 15 is movable here in the radial direction R and, perpendicularly thereto, is guided interlockingly in the receiving recess 16.

In the embodiment shown, the blocking element 14 is a linearly movable slide 17. The slide 17 is received in a further receiving recess 18 provided for this purpose in the handle device 2.

In the present case, both the actuation element 13 and the blocking segment 14 are mounted movably on the fixed handle part 6.

The operative connection between the movable handle part 7 and the blocking element 14 can in principle be embodied in different ways. In the embodiment shown, the movable handle part 7 is mounted on the fixed handle part 6 pivotably about a pivot pin 19, and the blocking element 14 has a driver pin 20 which is oriented parallel to the pivot pin 19 and which interacts with a driver groove 21 introduced into the end face of the movable handle part 7. In the working position, the movable handle part 7 is moved towards the fixed handle part 6 in a manner pivoting about the pivot pin 19. In the enabling position, the movable handle part 7 is moved away from the fixed handle part 6 about the pivot pin 19. The pivot pin 19 is oriented orthogonally with respect to the axial direction A and the radial direction R. In other words, the pivot pin 19 is oriented parallel to a transverse axis (not shown in detail) of the handle device 2 and/or of the shaft 3. The same applies as regards the driver pin 20 of the blocking element 14, oriented parallel to the pivot pin 19. The driver groove 20 and the driver pin 21 interact in a sliding movement in the circumferential direction of the driver pin 21. The blocking element 14 is slidably movable in the axial direction A and is held interlockingly in the further receiving recess 18 in the radial direction R. In this way, a pivoting movement of the handle part 7 in the direction of the working position causes a distal linear movement of the blocking element 14.

In the embodiment shown, the movable handle part 7 is operatively connected to the push-pull element 5, for transmission of force and motion, exclusively by the blocking element 14. Accordingly, the blocking element 14 in the embodiment shown has a particularly advantageous multiple function. On the one hand, the blocking element 14 serves for the already described blocking of the actuation element 13. On the other hand, the blocking element 14 additionally serves as a mechanical transmission element for transmitting the actuating movement and/or actuating force of the movable handle part 7 to the push-pull element 5 and thus to the forceps jaw 4.

Figures 4, 5:
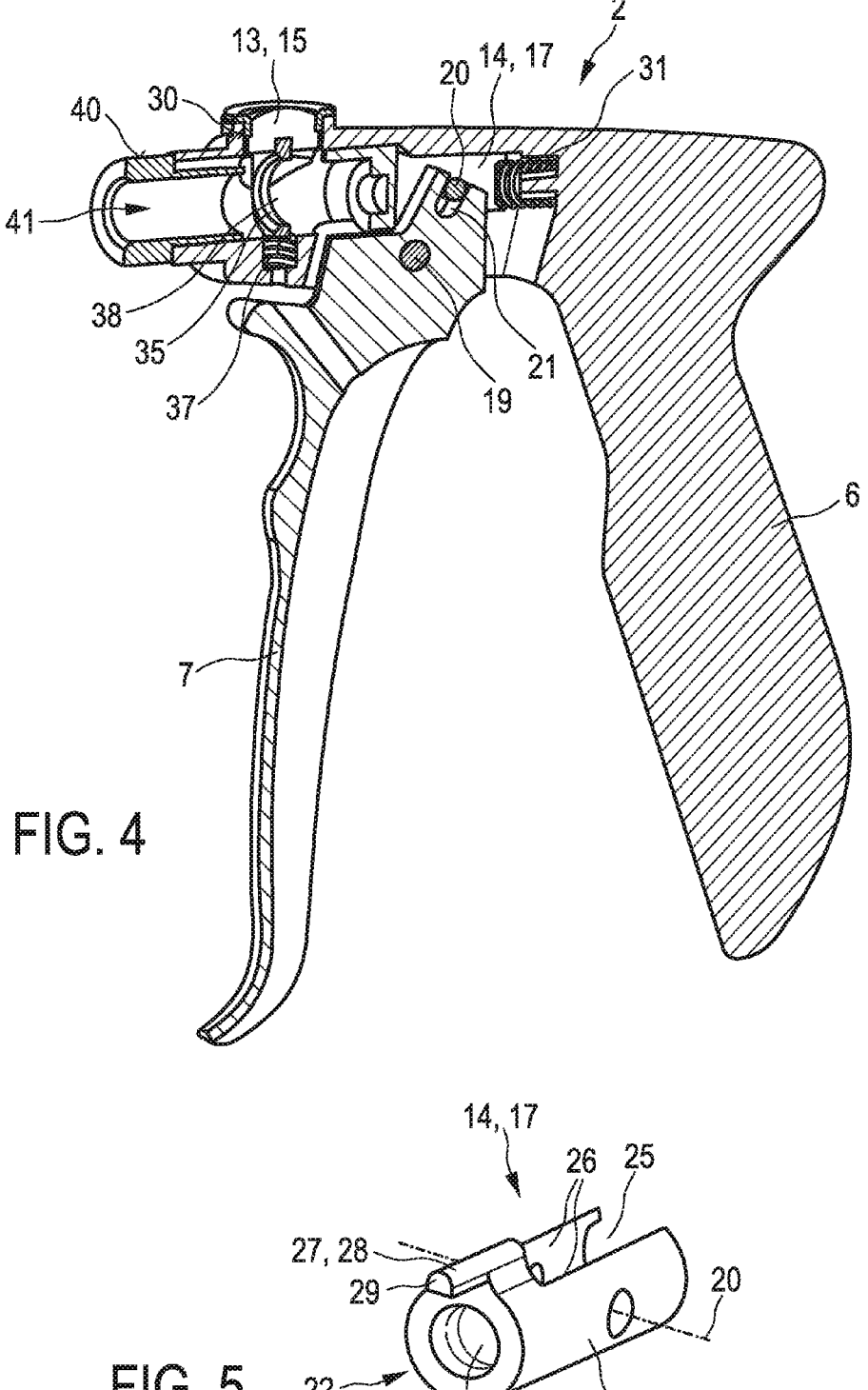
FIG. 4 shows a perspective longitudinal sectional view of the handle device of the medical instrument according to FIGS. 1 to 3.
FIG. 5 shows a schematic perspective view of a blocking element assigned to the handle device.

For the operative connection to the push-pull element 5, the blocking element 14 has a distally arranged supporting portion 22 (FIG. 5). The proximal end 11 of the push-pull element 5 is supported in the axial direction A on the supporting portion 22. In the present case, the proximal end 11 is additionally received interlockingly on the supporting portion 22 in the radial direction R. For this purpose, the supporting portion 22 has a recess 23 extending in the proximal direction starting from the distal end face of the blocking element 14. The proximal end 11 is plugged releasably into the recess 23 in the proximal direction.

Further features of the blocking element 14 of the present embodiment are shown in FIG. 5. The blocking element 14 in the present case has a cylindrical main portion 24 which extends along the axial direction A between the distal supporting portion 22 and a proximal end face (not shown in detail). The main portion 24 has a cutout 25 extending continuously in the radial direction R between an upper face and a lower face. The upper end face of the movable handle part 7, provided with the driver groove 21, engages in the cutout 25 in the radial direction R and is arranged in the transverse direction between mutually opposite side walls 26 of the main portion 24. For the form-fit blocking of the actuation element 13, the blocking element 14 has a blocking portion 27. The blocking portion 27 can also be designated as a form-fit portion. The blocking portion 27 protrudes from the main portion 24 in the distal direction. In the present case, the blocking portion 27 is a distally protruding blocking finger 28. In the blocking position, the blocking portion 27 engages under the actuation element 13 and in this way blocks a movement of the actuation element 13 into the release position. The driver pin 20 extends in the transverse direction through the main portion 24 and/or the cutout 25.

In the embodiment shown, the blocking element 14 is produced in one piece from a plastic material. Alternatively, the blocking element can be produced from metal and/or in multiple pieces.

It will be seen for example from FIGS. 3 and 4 that the mobility of the blocking element 14, hence also of the movable handle part 7, is blocked in the radially inwardly relocated release position of the actuation element 13. The reason is that, in the release position (not shown in detail), the actuation element 13 is relocated radially inwards in such a way that the blocking element 14 is prevented from moving in the distal direction. In the release position, an outer circumference 30 of the actuation element 13 functions as a stop for the blocking element 14, more precisely for an end face 29 of the blocking portion 27. Accordingly, the actuation element 13 also has a particularly advantageous multiple function. On the one hand, the actuation element 13 serves to actuate the locking device 8 in order to release the lock. On the other hand, the actuation element 13 additionally functions as a (further) blocking element for interlockingly blocking the mobility of the blocking element 14 and hence also of the movable handle part 7. This prevents the movable handle part 7 from being able to be actuated during the actuation of the actuation element 13, i.e. upon release of the locking.

In the embodiment shown, the blocking element 14 is pretensioned with spring loading in the direction of the blocking position by a first spring element 31 arranged on the handle device 2. As a result of this pretensioning, the blocking element 14, in the dismantled disassembly state of the medical forceps 1 (see FIG. 8), is always relocated to the blocking position. On account of the existing operative connection to the blocking element 14, the movable handle part 7 is pretensioned indirectly with spring loading by the first spring element 31. This pretensioning acts in the direction of the working position. As a result, the movable handle part 7 in the disassembly state is always relocated to the working position (see FIG. 8). The first spring element 31 acts in the axial direction A on the blocking element 14. The first spring element 31 is supported in the proximal direction on the fixed handle part 6 and in the distal direction on a proximal end face (not shown in detail) of the blocking element 14. In the embodiment shown, the first spring element 31 is a compression spring. The spring element 31 is designed as a helical spring.

For the sake of completeness, it is noted that the pretensioning of the blocking element 14 and of the movable handle part 7 is not implemented in the drawing in FIG. 4. In other words, the movable handle part 7 in the drawing is fixed in the rest position counter to the pretensioning of the first spring element 31. The same applies, mutatis mutandis, to the blocking element 14.

Said pretensioning by the first spring element 31 prevents the actuation element 13 from being able to be relocated to the release position in the disassembly state. Correct assembly of the shaft 3 on the handle device 2 is assisted in this way, as will be described in more detail below.

When the shaft 3 and the handle device 2 are connected to each other, i.e. the medical forceps 1 is in the assembly state (FIGS. 1, 3, 6, and 7), a second spring element 32, in addition to the first spring element 31, acts on the blocking element 14. The second spring element 32 (FIG. 2) causes a spring-loaded pretensioning of the blocking element 14 in the direction of the enabling position. Here, the second spring element 32 is stronger, i.e. causes a stronger pretensioning, than the first spring element 31. In other words, the pretensioning of the blocking element 14 is mainly in the direction of the enabling position. In this way, the blocking element 14 in the assembly state, and with non-actuation of the movable handle part 7, is always relocated to the enabling position. On account of the operative connection to the blocking element 14, the movable handle part 7 is pretensioned with spring loading indirectly by the second spring element 32. The pretensioning acts in the direction of the rest position. This despite the likewise present pretensioning by the first spring element 31.

The second spring element 32 is arranged on the shaft 3. Accordingly, the second spring element 32 acts on the blocking element 14 only when the shaft 3 is mounted on the handle device 2.

In the embodiment shown, the second spring element 32 functions at the same time as a restoring spring for the push-pull element 5. The second spring element 32 acts on the blocking element 14 indirectly via the push-pull element 5. The second spring element 32 is arranged at the distal end 10 of the shaft 3. The second spring element 32 acts in the axial direction A on the push-pull element 5 and thus also on the blocking element 14. The second spring element 32 is supported in the proximal direction on the distal end 12 of the push-pull element. This support can be direct or indirect. In the distal direction, the second spring element 32 is supported on a structural part (not shown in detail) assigned to the forceps jaw 4. The design details of the forceps jaw 4 are immaterial as regards the function of the second spring element 32, and further explanations in this connection can therefore be omitted. The second spring element 32 in the present case is a compression spring. The second spring element 32 is designed as a helical spring.

As is further shown in FIG. 2, the forceps jaw 4 in the embodiment shown is formed between a first jaw part 33 and a second jaw part 34. In the open position (FIG. 2), the first jaw part 33 and the second jaw part 34 are moved away from each other In the closed position (FIG. 1), the two jaw parts 33, 34 are moved towards each other.

The opening and/or closing of the forceps jaw 4 takes place under the effect of the push-pull element and in a manner known to a person skilled in the art. In the present case, a distal movement of the push-pull element 5 causes closing of the forceps jaw 4. A proximal movement of the push-pull element causes opening of the forceps jaw 4. Further explanations in this connection are not needed in respect of the present invention.

To lock the shaft 3 on the handle device 2, the locking device 8 in the embodiment shown has a spring-loaded latch 35. For interaction with the latch 35, the shaft 3 has a notch 36 at its proximal end 9. In the assembly state and in the non-actuated rest position of the actuation element 13, the latch 35 engages interlockingly in the axial direction A in the notch 36. By an actuation of the actuation element 13, the latch 35 can be disengaged from the notch 36 in the radial direction R. In the present case, the latch 35 is pretensioned inwards by spring loading in the radial direction R. For this purpose, a third spring element 37 is present. The third spring element 37 acts indirectly on the actuation element 13 via the latch 35. The actuation element 13 is pretensioned with spring loading by the third spring element 37 counter to a movement into the release position.

In the embodiment shown, the notch 36 is an annular groove 39 extending in the circumferential direction of the shaft 3. The annular groove 39 is formed at the proximal end 11 of the shaft 3. Furthermore, the latch 35 has a throughbore 38, through which the push-pull element 5 extends.

The locking, more precisely the latch-notch connection between latch 35 and notch 36, counteracts an unwanted release of the shaft 3 from the handle device 3, and vice versa. For connection to the shaft 3, the handle device 2 in the present case has a distally arranged outer cone 40 with a receiving bore 41. For connection to the handle device 2, the shaft 3 has an inner cone 42. In the assembly state, the outer cone 40 and the inner cone 42 are plugged together in an axially releasable manner. The plug-in connection thus formed is locked releasably by the locking device 8.

In the embodiment shown, the shaft 3 is in multiple parts and has a shaft tube 43, a shaft attachment 44 and a shaft extension 45 (FIG. 3). The shaft tube 43, the shaft attachment 44 and the shaft extension 45 are joined together in a manner known to a person skilled in the art. In the present case, the inner cone 42 is formed on the shaft attachment 44. The notch 36 is formed on the shaft extension 45. In the assembly state, the shaft extension 45 is inserted into the receiving bore 41 and extends through the through-bore 38. It will be appreciated that the present design of the shaft 3 is shown as an example and is not essential in terms of the invention. Indeed, a one-part design of the shaft is also conceivable in principle.

Figures 8, 9:
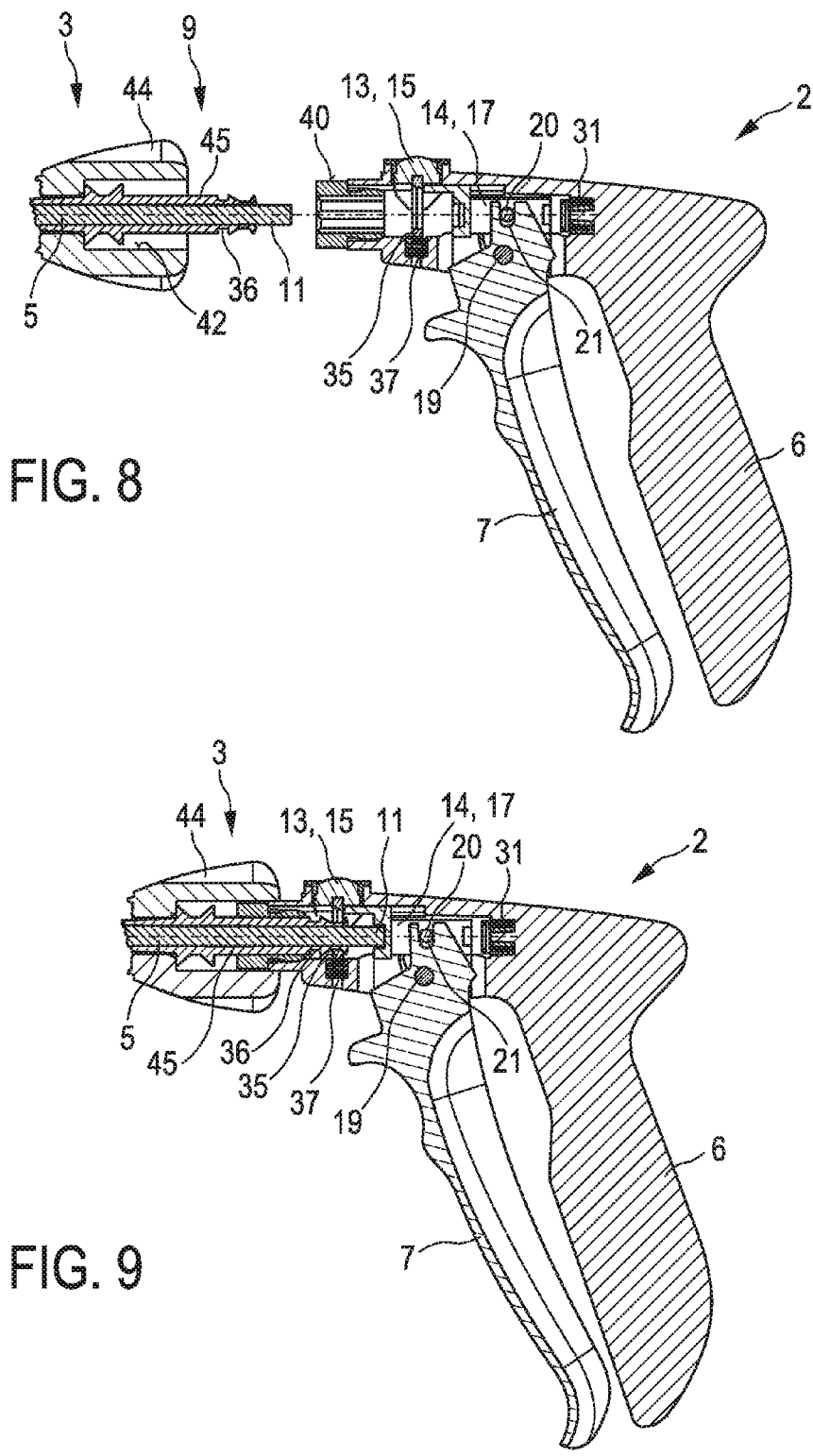
FIGS. 8, 9 and 10 show, in each case in a view corresponding to FIGS. 6 and 7, the medical instrument in different configurations in order to illustrate assembly/disassembly of the shaft on/from the handle device.
Figure 10:
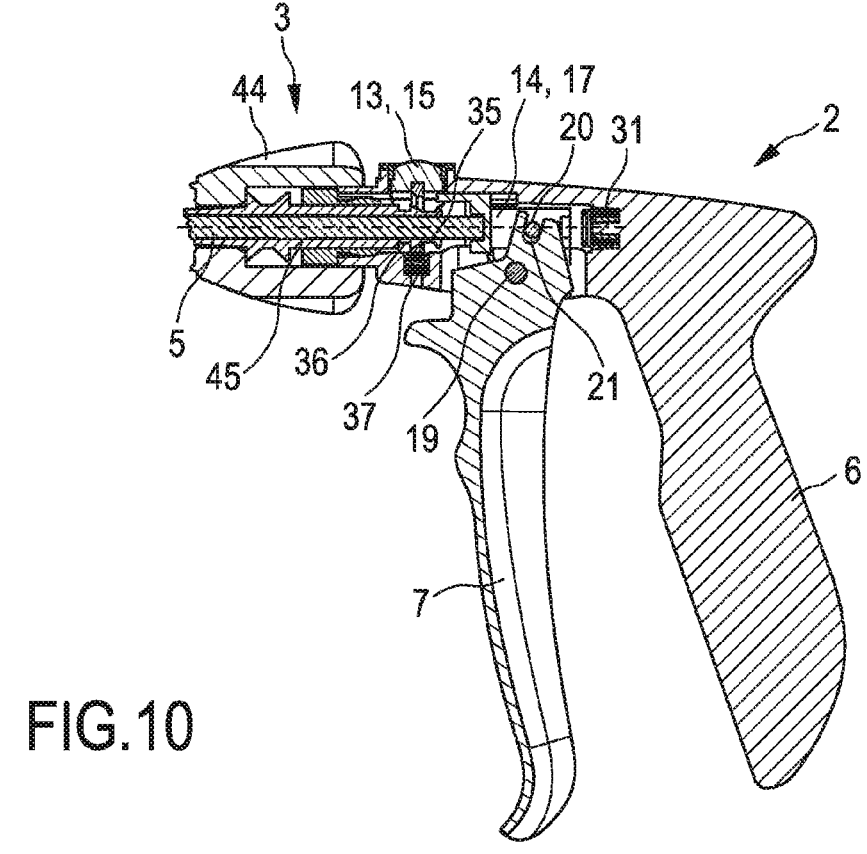

The function of the medical forceps 1 is explained in detail below with reference to FIGS. 6 to 10. In particular, the function of the blocking element 14 and the interaction of the latter with the further components of the medical forceps 1 are described. The assembly state will be considered first (FIGS. 6 and 7). Thereafter the assembly/disassembly (FIGS. 8, 9 and 10).

FIG. 6 shows the medical forceps 1 in the assembly state and in a first configuration, which can also be designated as a non-actuated configuration. In the first configuration, the movable handle part 7 is in its rest position. The second spring element 32 acts in the proximal direction on the blocking element 14 via the push-pull element 5. The first spring element 31 acts in the distal direction on the blocking element 14. Since the spring force of the second spring element 32 is greater than the spring force of the first spring element 31, the spring-loaded pretensioning is predominantly in the proximal direction. As a result, the blocking element 14 is relocated/pretensioned into the enabling position. The movable handle part 7 is relocated/pretensioned into the rest position. The locking is active. Here, the latch 35 is placed into the notch 36 by the third spring element 37. The third spring element 37 effects indirectly, namely via the latch 35, a pretensioning of the actuation element 13 counter to a movement into the release position.

Starting from the first configuration, the actuation element 13 can be relocated into the release position. In this way, the latch 35 is moved outward in the radial direction R out of the notch 36. This causes a release of the locking. The shaft 3 can then be pulled away from the handle device 2 in the distal direction. In this way, the medical forceps 1 is disassembled and/or converted to its disassembly state (FIG. 8).

The disassembly state (FIG. 8) can also be designated as a third configuration. In this third configuration, the first spring element 31 causes the blocking element 14 to relocate to the blocking position. The movable handle part 7 is accordingly moved to its working position. The mobility of the actuation element 13 is interlockingly blocked by the blocking element 14.

Starting from the third configuration (FIG. 8), the shaft can be mounted again on the handle device 2. Such mounting is illustrated in FIGS. 9 and 10. To mount the shaft 3, the proximal end 9 of the latter is plugged together with the handle device 2 in the axial direction. In this way, the above-described plug-in connection between the outer cone 40 and the inner cone 42 is produced.

FIG. 9 shows a fourth configuration in which the shaft 3 and the handle device 2 are partially plugged together starting from the third configuration. In this fourth configuration, the shaft extension 45, together with the push-pull element 5, is plugged in the proximal direction into the receiving bore 41. The latch-notch connection between latch

35 and notch 36 is not yet established. Accordingly, there is still no locking of the (partial) plug-in connection. The proximal end 11 of the push-pull element 5 is already received on the supporting portion 22.

FIG. 10 shows a fifth configuration, in which the shaft 3 and the handle device 2 are plugged further together. Here, the shaft 3, together with the push-pull element 5, is relocated further in the proximal direction relative to the handle device 2. In this way, the blocking element 14 is pressed in the proximal direction, i.e. in the direction of its enabling position, under the effect of the proximal end 11 of the push-pull element 5. Accordingly, the movable handle part 7 is already relocated partially in the direction of its rest position. The actuation element 13 is interlockingly blocked by the blocking element 14 as before. The latch 35 is not yet placed into the notch 36.

By further plugging together of the shaft 3 and the handle device 2, the first configuration (FIG. 6), hence the assembly state, is obtained starting from the fifth configuration.

Starting from the assembly state and/or the first configuration, the medical forceps 1 can be actuated in order to open and/or close the forceps jaw 4 (FIG. 7, second configuration). In the present case, a relocation of the movable handle part 7 from the rest position to the working position causes closing of the forceps jaw 4. Pulling the movable handle part 7 towards the fixed handle part 6 has the effect that the movable handle part 7 is relocated anticlockwise about the pivot pin 19. On account of the interaction of the driver groove 21 and of the driver pin 20, this means at the same time that the blocking element 14 is relocated in the distal direction. In this way, on the one hand, the mobility of the actuation element 13 in the direction of the release position is interlockingly blocked. On the other hand, the blocking element 14 pushes the push-pull element 5 in the distal direction. In this way, the push-pull element 5 is relocated axially relative to the shaft 3 and to the forceps jaw 4 mounted distally on the shaft 3. The distal end 12 acts on the forceps jaw 4 in a force-transmitting and movement-transmitting manner, such that the forceps jaw 4 is closed. The axial movement of the push-pull element 5 in the distal direction takes place counter to the spring force of the second spring element 32. As soon as the actuation of the movable handle part 7 is stopped, the second spring element 32 causes a proximally directed restoring movement of the push-pull element 5, opening of the forceps jaw 4, relocation of the blocking element 14 into the enabling position, and relocation of the movable handle part 7 into the rest position. The first configuration is then once again adopted.

The invention claimed is:

1. A medical instrument comprising:
   a handle device with a fixed handle part, a movable handle part, and a locking device, the movable handle part being manually movable relative to the fixed handle part between a non-actuated rest position and an actuated working position;
   a shaft that is elongate, the shaft having a proximal end releasably locked on the handle device by the locking device;
   an instrument jaw arranged on a distal end of the shaft, the instrument jaw being movable between an open position and a closed position by an actuation of the movable handle part; and
   a push-pull element that is elongate and guided axially movably in the shaft and which, for force and movement transmission, is operatively connected proximally to the movable handle part and distally to the instrument jaw, the locking device comprising an actuation element that is movable manually into a release position in order to release the locking, and a blocking element that is operatively connected to the movable handle part, the blocking element being movable into a blocking position in the actuated working position of the movable handle part, in which the blocking element interlockingly blocks mobility of the actuation element, the blocking element also being movable into an enabling position in the non-actuated rest position of the movable handle part, in which mobility of the actuation element is enabled, wherein the blocking element is pretensioned with spring loading in a direction of the blocking position by a first spring element arranged on the handle device, and, in a locked state of the shaft, is pretensioned with spring loading in a direction of the enabling position by a second spring element arranged on the shaft, and wherein the second spring element causes greater pretensioning than the first spring element.

2. The medical instrument according to claim 1, wherein the actuation element in the release position blocks mobility of the blocking element into the blocking position and/or blocks mobility of the movable handle part into the actuated working position.

3. The medical instrument according to claim 1, wherein the actuation element is movable in a radial direction of the push-pull element, and the blocking element is movable in an axial direction of the push-pull element.

4. The medical instrument according to claim 1, wherein the actuation element is a push button which is pressable into the release position, and the blocking element is a linearly movable slide which, in the blocking position, is slid at least partially under the push button.

5. The medical instrument according to claim 1, wherein the movable handle part is mounted on the fixed handle part pivotably about a pivot pin, and the blocking element has a driver pin oriented parallel to the pivot pin, the drive pin interacting with a driver groove introduced into an end face of the movable handle part.

6. The medical instrument according to claim 1, wherein the movable handle part acts on a proximal end of the push-pull element in a force-transmitting and movement-transmitting manner by way of the blocking element.

7. The medical instrument according to claim 6, wherein the blocking element has a distally arranged supporting portion on which the proximal end of the push-pull element is supported in an axial direction and/or is received interlockingly in the radial direction.

8. The medical instrument according to claim 1, wherein the locking device has a spring-loaded latch that engages interlockingly in a notch of the shaft in an axial direction and is disengageable from the notch by the actuation element.

* * * * *